United States Patent
Kwon et al.

(10) Patent No.: US 6,620,938 B1
(45) Date of Patent: Sep. 16, 2003

(54) COMPOUNDS THAT INHIBIT GRB2-SHC BINDING AND PROCESS FOR PREPARING SAME

(75) Inventors: Byoung-Mog Kwon, Daejeon (KR); Mi-Young Han, Daejeon (KR); Kwang-Hee Son, Daejeon (KR); Sung-Uk Kim, Daejeon (KR); Hyae-Kyeong Kim, Daejeon (KR); Kyung-Sook Bae, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 09/573,632

(22) Filed: May 12, 2000

(30) Foreign Application Priority Data

Dec. 23, 1999 (KR) .............................. 99-61092

(51) Int. Cl.⁷ ................. C07D 217/12; A61K 31/47
(52) U.S. Cl. ........................ 546/147; 514/307
(58) Field of Search ................... 546/147; 514/307

(56) References Cited

PUBLICATIONS

Chemical Abstracts 133:172122, Nam, 2000.*

* cited by examiner

*Primary Examiner*—D. Margaret Seaman
(74) *Attorney, Agent, or Firm*—Katten Muchin Zavis Rosenman

(57) ABSTRACT

A novel compound of the formula(I) having a high inhibitory activity against Grb2-Shc binding may be useful for the prevention and treatment of intracellular signal transmission-related diseases.

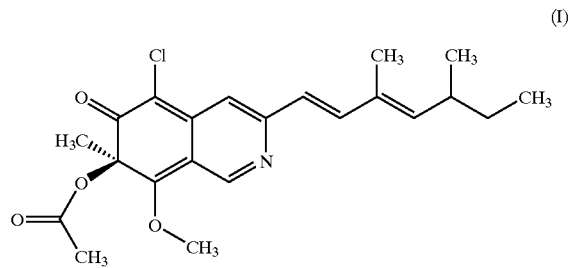

(I)

2 Claims, 5 Drawing Sheets

COMPOUNDS THAT INHIBIT GRB2-SHC BINDING AND PROCESS FOR PREPARING SAME

FIELD OF THE INVENTION

The present invention relates to a compound that inhibits the binding between Grb2(Growth factor receptor-binding protein-2) and Shc(Src homology and collagen protein) with a consequential effect of suppressing cancer cell proliferation or differentiation; to a process for isolating said compound from Penicillium multicolor F1753; and to a pharmaceutical composition containing same.

BACKGROUND OF THE INVENTION

Extensive molecular-biochemical studies on normal and transformed cells have revealed that abnormality in the signal transmission involved in the growth and division of cells causes cancer, and also that proteins produced by the expression of oncogenic genes regulate the growth and division of cells. Namely, it has been reported that growth factors, growth factor receptors, intracellular tyrosine phosphorylase's, Ras proteins, adaptor proteins, transcription factors and the like take part in the intracellular signal transmission and play crucial roles in cell proliferation (see Alexander, L. Eur. J. Biochem. 226, 1–13, 1994).

A series of intracellular signal transmission steps involving Ras protein occur as follows. A signal transmitting substance binds to a growth factor receptor, which causes phosphorylation of tyrosine on the receptors The phosphotyrosine of the activated receptor is recognized by Shc(Src homology and collagen protein), one of adaptor proteins containing SH2 domains, and then, Shc binds to Grb2 (Growth factor receptor-binding protein-2) which contains an SH2 domain in the center and SH3 domains at both ends. Grb2 serves to couple the tyrosine-phosphorylated receptor to an important downstream signaling protein Ras, and finally the Ras protein relays the signals delivered intracellularly by such receptors into the cell interior to stimulate cell proliferation and differentiation.

As mentioned above, it is believed that various factors are involved in the intracellular signal transmission and when such signal transmission fails due to disorders in one or more signal transmitting factors, the cell growth becomes abnormal to cause various diseases including cancer.

The present inventors have carried out extensive studies to identify a compound which is capable of intercepting abnormal signal transmission, and have discovered that specific compounds isolated from Penicillium multicolor F1753 exhibit a high inhibitory activity against the binding between Grb2 and Shc.

SUMMARY OF THE INVENTION

Accordingly, it is an object of the present invention to provide a novel compound which has a high inhibitory activity against the binding between Grb2 and Shc.

It is another object of the present invention to provide a process for isolating and purifying said compounds from Penicillium microorganisms.

It is a further object of the present invention to provide a pharmaceutical composition containing an effective amount of said compounds.

In accordance with one aspect of the present invention, there is provided a novel compound of formula(I) for inhibiting the binding between Grb2and Shc:

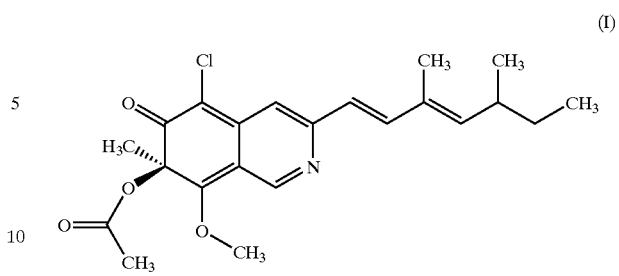

(I)

BRIEF DESCRIPTION OF THE DRAWINGS

The above and other objects and features of the present invention will become apparent from the following description of the invention taken in conjunction with the following accompanying drawings, wherein.

DETAILED DESCRIPTION OF THE INVENTION

Figure 1:
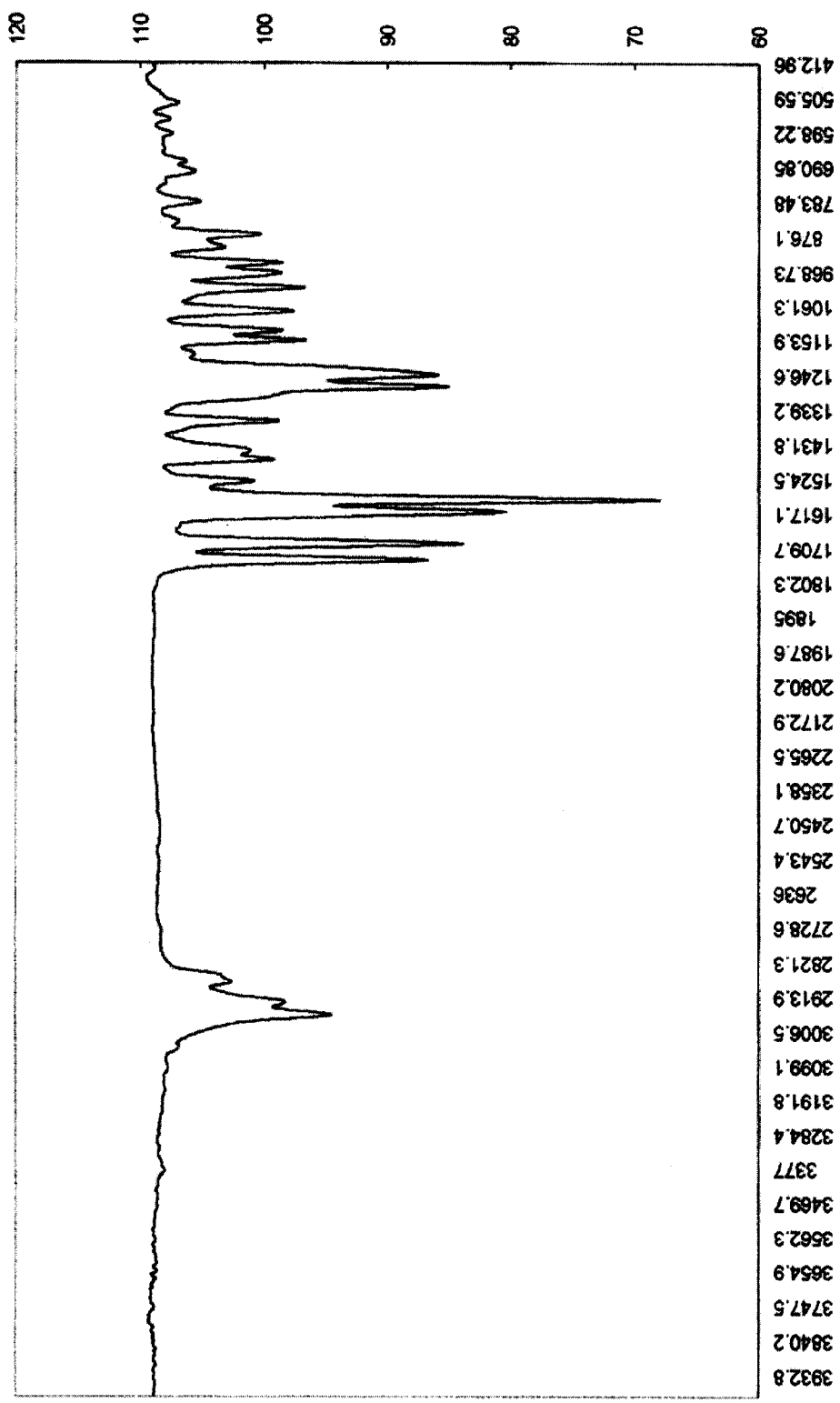
FIG. 1 shows an IR spectrum of the compound of formula (I)

In accordance with one aspect of the prevent invention, the compound of formula(I) of the present invention is extracted from a culture solution of Penicillium multicolor F1753 by employing suitable organic solvents and purified according to a common procedure as further described below.

In accordance with another aspect of the present invention, there is provided a process for the preparation of the compound of formula(I) comprising the steps of: (a) dividing a culture solution of Penicillium multicolor F1753 into a cell body and a culture fluid fraction, and extracting them separately with organic solvents; (b) combining the extract solutions and evaporating the solvents therefrom to obtain a concentrate, followed by extracting the concentrate with another organic solvent and removing said another organic solvent to obtain an extract; (c) subjecting the extract to silica gel column chromatography using a mixture of hexane and ethyl acetate as an eluent to obtain a refined fraction; and (d) subjecting the fraction to reverse chromatography using a mixture of water and methanol as an eluent.

Representative examples of the organic solvents used in step (a) in accordance with the present invention include acetone, chloroform, ethanol and methanol, among which acetone is preferred for the extraction of the cell body fraction, while chloroform is preferably employed in the extraction of the culture fluid fraction. Representative examples of the organic solvent used in step (b) in accordance with the present invention include methylene chloride and chloroform.

In practicing the process of the present invention, Penicillium multicolor F1753 is inoculated to a conventional medium for Penicillium strain and cultured at a temperature ranging from 20 to 30° C. for 1 to 5 days with shaking, the resulting culture solution is used in inoculating a conventional medium for producing Penicillium, and cultured at a temperature ranging from 20 to 30° C. for 3 to 7 days with shaking. The culture solution thus obtained is divided into a cell body and a culture liquid fraction, which are respectively extracted with acetone and chloroform at room temperature. The extract solutions are combined, the solvents are evaporated under a reduced pressure and the residue is extracted with a 10 to 15 fold volume of methylene chloride at room temperature. After removing the solvent, the extract is subjected to silica gel column chromatography twice in sequence using a mixture of hexane and ethylacetate as an eluent to obtain a refined fraction, which is subjected to reverse chromatography using a mixture of water and methanol as an eluent to obtain active materials which include the novel compound of formula(I), sklerothiorine of formula(II) and isochromopilone IV of formula(III) (see Doherty A. M. et al., *J Antibiotics* 48, 913–923(1995); Omura, S. et al., *J Antibiotics* 48, 696–702(1995)). It has been reported that sclerotiorine of formula(II) has phospholipase $A_2$ inhibiting activity and isocluomopilone IV of formula(III) is useful as an ACAT inhibiting agent.

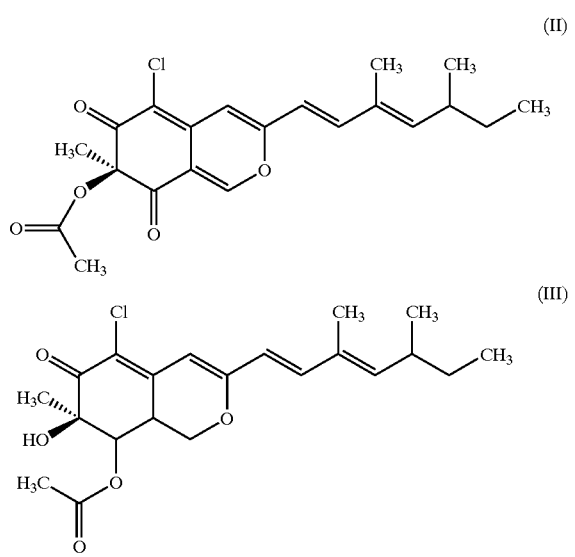

The compounds of formulae(I), (II) and (III) obtained in accordance with the inventive process exhibit varying degrees of inhibitory activity against Grb2-Shc binding, the concentration required for inhibiting the Grb2-Shc binding by 50%($IC_{50}$) being about 6, 12 and 11 μM, respectively.

The present invention also includes within its scope a pharmaceutical composition comprising one or more of the compounds of formulae(I), (II) and (III) as an active ingredient, in association with pharmaceutically acceptable carriers, excipients or other additives, if necessary. The pharmaceutical composition of the present invention may be useful as an anticancer agent for suppressing the expression of oncogenic genes and as an agent for preventing and treating intracellular signal transmission-related diseases, e.g., asthmas, transmission of cancer, cardiovascular disease and autoimmune disease.

The pharmaceutical composition of the present invention may be formulated according to any one of the conventional procedures in the form of a tablet, pill, powder, sachet, elixir, suspension, emulsion, solution, syrup, aerosol, soft and hard gelatin capsule, sterile injectable solution, sterile packaged powder and the like.

The pharmaceutical composition of the present invention can be administered by a variety of routes including oral, transdermal, subcutaneous, intravenous and intramuscular introduction. A typical daily dose of the active ingredient may range from 0.1 to 50 mg/kg body weight, preferably 1 to 10 mg/kg body weight, and can be administered in a single dose or in divided doses. However, it should be understood that the amount of the active ingredient actually administered ought to be determined in light of various relevant factors including the condition to be treated, the chosen route of administration, the age and weight of the individual patient, and the severity of the patient's symptom; and, therefore, the above dose should not be intended to limit the scope of the invention in any way.

The following Examples are given for the purpose of illustration only, and are not intended to limit the scope of the invention.

EXAMPLE 1

Isolation and Identification of Microorganisms

Soil samples collected from Chilgapsan, Choongchungnamdo, Korea, were dispersed in sterilized water, spread on a medium (yeast extract 0.3%, malt extract 0.3%, dextrose 1% and peptone 0.5%), and incubated at 28° C. for 5 days, followed by collecting mold therefrom.

The mold strain thus isolated was identified to be Penicillium multicolor based on its morphological and physiological characteristics according to the known test methods (Williams, S. T., et al., *Beryer's Mannual of Systematic Bacteriology*, Vol. 4, 2451–2492, Williams and Wilkins Co., Baltimore; Japan Research Institute of Streptococcus, *Identification test Method of Streptococcus*, p.1–160(1985), Bureau of Japan Research Institute of Streptococcus, Tokyo; and Hasegawa Takeji, *Identification of Microorganism Sorts*, p.155–437(1981), Academy Publication Center, Tokyo).

This mold, designated Penicillium multicolor F1753, was deposited on Apr. 27, 2000 with the Korean Collection for Type Cultures (KCTC) (Address: Korea Research Institute of Bioscience and Biotechnology(KRIBB), #52, Oun-dong, Yusong-ku, Taejon, 305–333, Republic of Korea) under the accession number, KCTC 0771BP, in accordance with the terms of Budapest Treaty on the International Recognition of the Deposit of Microorganisms for the Purpose of Patent Procedure.

EXAMPLES 2

Isolation and Purification of Compounds(I), (II) and (III)

50 ml of a sterilized culture medium (glucose 2%, yeast extract 0.2%, polypeptone 0.5%, phosphate(I) 0.1%, magnesium sulfate 0.05%; pH 7.2) was placed in a 500 ml flask, inoculated with Mold F1753 obtained in Example 1 and cultured at 25.5° C. for 2 days with shaking. Then, 4 ml of the culture solution was used in inoculating 150 ml of a sterilized preparative medium (water-soluble starch 2%, bacto-soyton 0.4%, Pharma media 0.5%, phosphate(II) 0.1%, magnesium sulfate 0.05%, sodium chloride 0.2%, calcium carbonate 0.3%, ferrous sulfate 0.002%, manganesium chloride 0.001%, zinc sulfate 0.001% and cobalt chloride 0.0005%; pH 6.0) placed in a 1 l flask and cultured at 25.5° C. for 5 days with shaking.

The culture solution thus obtained was separated into cell body and culture liquid fractions. Then, the cell body fraction was extracted with 200 ml of acetone, while 600 ml of the culture liquid fraction was extracted with an equal volume of chloroform at room temperature. The organic extract layers were combined, evaporated under a reduced pressure to obtain a concentrate, which was subsequently extracted with 300 ml of methylene chloride at room temperature over a period of 1 hour. After removing the solvent, the residue was subjected to silica gel column chromatography(column: Merck, Kieselgel 60, 230–400 mesh, Art 9385), using a mixture of hexane and ethylacetate (4:6) as an eluent. The same silica gel column chromatographic procedure was repeated one more time to obtain a refined fraction. The fraction was subjected to reverse chromatography(column: Merck Lichroprep, RP-18, 60~63 μm, Art 13900), using a mixture of water and methanol(2:8) as an eluent to obtain Compounds(I), (II) and (III) at yields of 1.7 mg, 2 mg and 0.8 mg per 1 l of culture solution of Penicillium multicolor F1753, respectively.

EXAMPLE 3

Physicochemical Analysis of Compounds(I), (II) and (III)

1) Each of Compounds(I), (II) and (III) obtained in Example 2 was dissolved in 100% methanol and analyzed with a UV-Vis spectrophotometer. Observed for Compound (I) were absorption maxima at 286 nm and 364 nm, and a slight shoulder at around 271 nm.

2) The molecular weight was determined by High-Resolution Electron Impaction(HREI)-MS, and the result showed the following molecular formula; Compound(I) (molecular weight: measured 403.1576, calculated for $C_{22}H_{26}NO_4Cl$: 403.1552); Compound(II)(molecular weight: measured 390.1219, calculated for $C_{21}H_{23}O_5Cl$: 390.1234); and Compound(III)(molecular weight: measured 394.1549, calculated for $C_{21}H_{27}O_5Cl$: 394.1548).

3) IR studies conducted with an Bio-Rad Win-IR spectroscope showed characteristic peaks at 2962, 2928, 2872, 1743, 1697, 1611, 1579, 1278 and 1245 $cm^{-1}$ for Compound (I); at 1741, 1726, 1669, 1630, 1621 and 1581 $cm^{-1}$ for Compound(II); and at 3430, 2960, 2930, 1870, 1750; 1670, 1560 and 1270 $cm^{-1}$ for Compound(III). The above results suggest that Compounds(I), (II) and (III) all contain such functional groups as aromatic C=C (1600 to 1575 $cm^{-1}$), olefinic C=C (1670 to 1600 $cm^{-1}$), CH (3000 to 2800 $cm^{-1}$), esteric C=O (1750 to 1730 $cm^{-1}$) and conjugated C=O (1680 to 1630 $cm^{-1}$). Compounds(I) further has C-N (1370 to 1250 $cm^{-1}$) and Compound(III), OH (3525 to 3200 $cm^{-1}$). An IR spectrum of Compound(I) is shown in FIG. 1.

Figure 2:
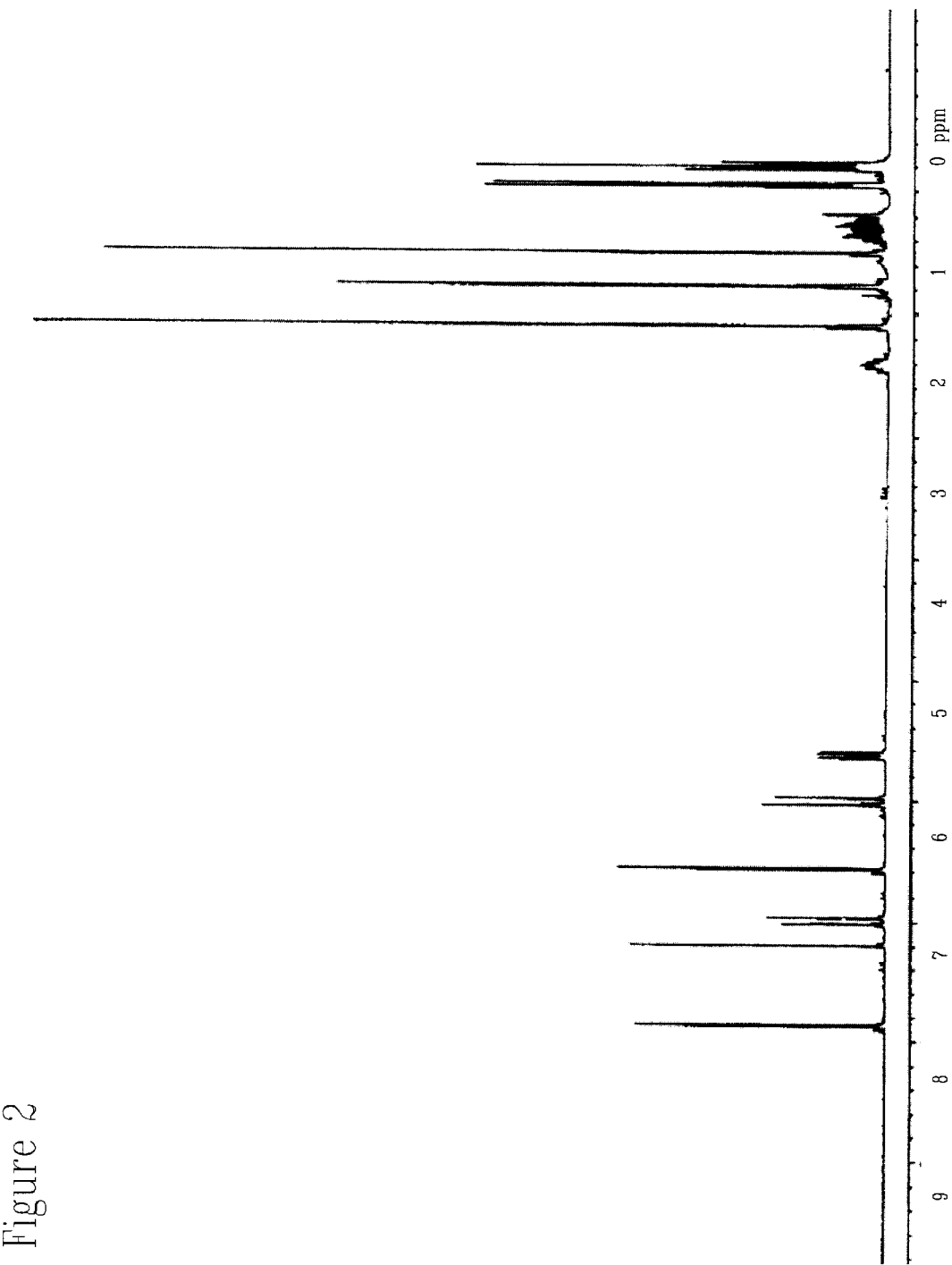
FIG. 2 provides an $^1$H-NMR spectrum of the compound of formula(I)
Figure 3:
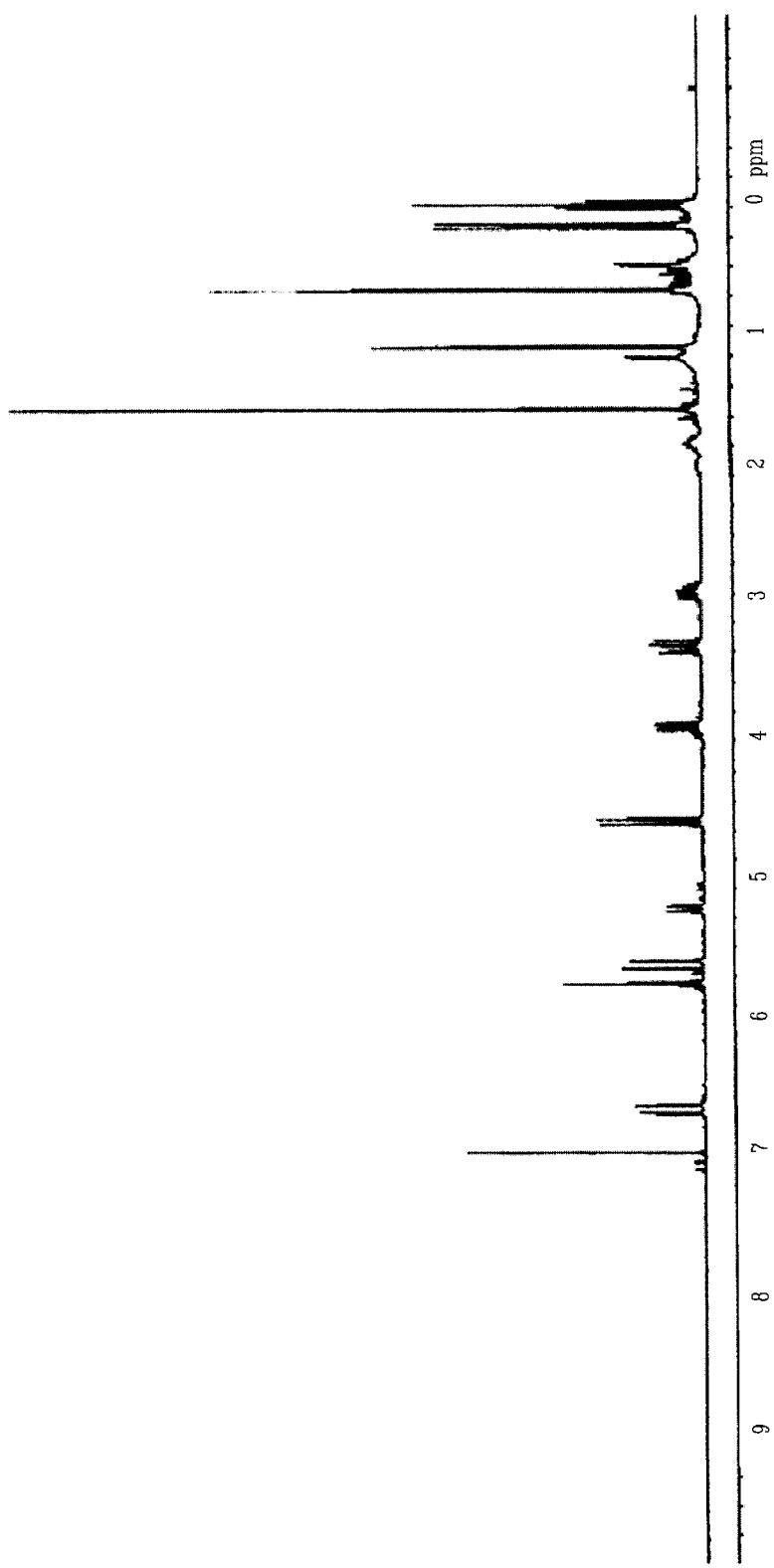
FIG. 3 displays an $^1$H-NMR spectrum of the compound of formula(II)
Figure 4:
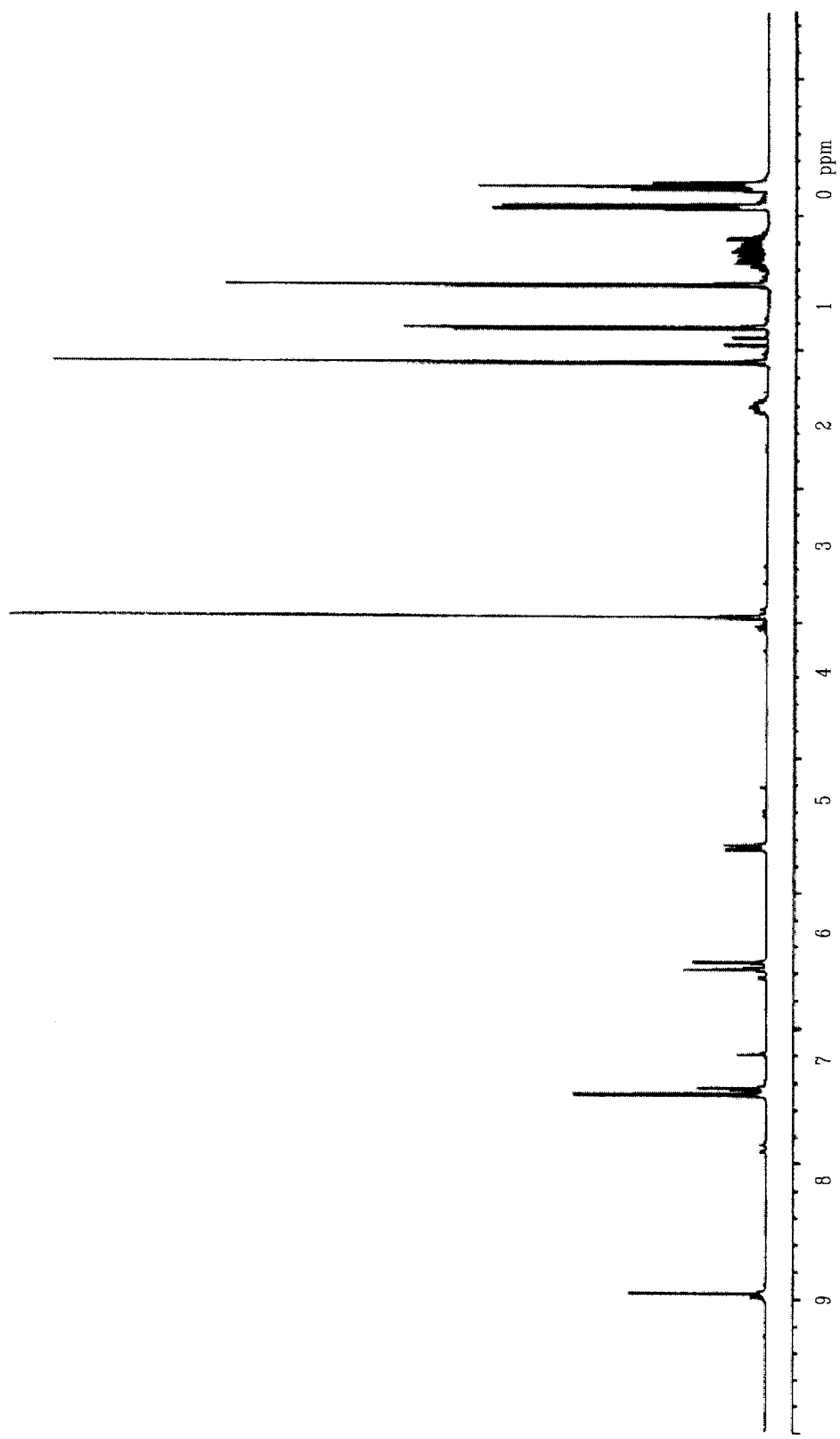
FIG. 4 depicts an $^1$H-NMR spectrum of the compound of formula(II)
Figure 5:
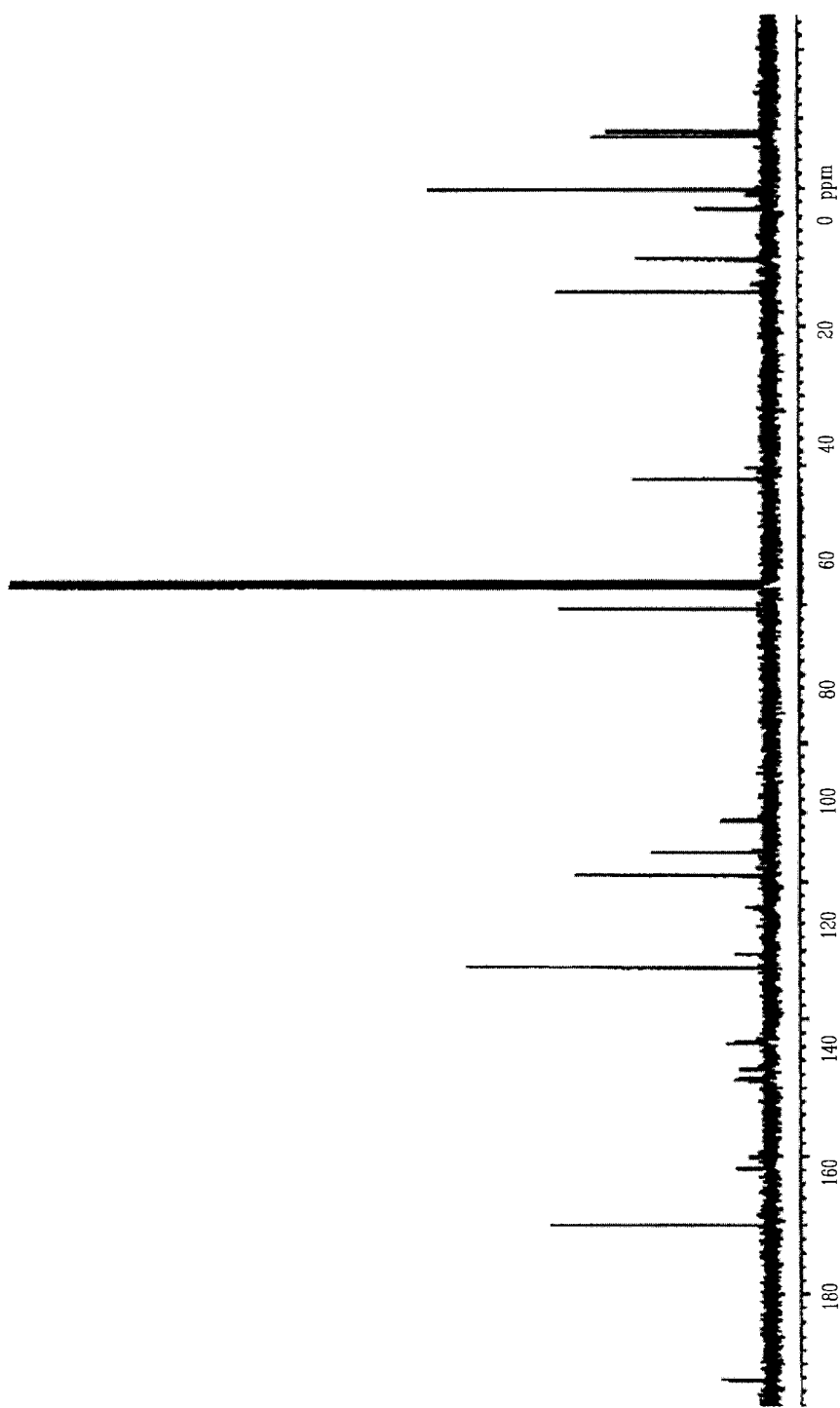
FIG. 5 represents a $^{13}$C-NMR spectrum of the compound of formula(I).

4) $^1H$, $^{13}C$, DEPT, $^1H$—$^1H$ COSY, HMQC and HMBC NMR analyses were carried out (see FIGS. 2, 3 and 4 for $^1H$-NMR spectra of Compounds(I), (II) and (III), respectively, and FIG. 5, $^{13}C$-NMR spectrum of Compound (I)). NMR data showed that Compounds(I), (II) and (III) are azapilones.

Based on the above-mentioned spectral data and physicochemical characteristics shown in Table 1, the structures of Compounds(I), (II) and (III) was unequivocally settled. Compounds(II) and (III) are sclerotiorine and isochromopilone, respectively, which are known compounds, while Compound(I) is a novel compound.

TABLE 1

|  | Compound(I) | Compound (II) | Compound (III) |
| --- | --- | --- | --- |
| Appearance | Light yellow gum | Yellow powder | Yellow powder |
| HREI-MS[M⁻] | 403 | 390 | 394 |
| Molecular formula | $C_{22}H_{26}NO_4Cl$ | $C_{21}H_{23}O_5Cl$ | $C_{21}H_{27}O_5Cl$ |
| UV $\lambda_{max}$(MeOH) | 286 (18000) | 285 (9100) | 249 (4500) |
|  | 364 (24000) | 363 (21000) | 340 (7800) |
| Rf value (hexane:EA = 15:5) | 0.46 | 0.35 | 0.19 |
| Soluble | CHCl₃, EtOAc, MeOH | CHCl₃, EtOAc, MeOH | CHCl₃, EtOAc, MeOH |
| Insoluble | H₂O | H₂O | H₂O |
| $[\alpha]_D^{20}$ | +110 (c 0.1, MeOH) | +480 (c 0.04, EtOH) | −340 (c 0.2, MeOH) |
| Melting point(° C.) | Liquid phase having heavy viscosity | 200~205 | 83~85 |

EXAMPLE 4

Assay for Grb2-Shc Binding Inhibiting Activity

The activity of the inventive compound in inhibiting Grb2-Shc binding was determined in accordance with the scintillation proximity assay method by way of measuring the extents of competitive bindings of [$^3H$]propionylated-hShc peptide and the inventive compound toward Grb2.

Added to a 1.5 ml eppendorf tube were 10 μl of 0.3 μg GST-Grb2 fusion protein(Santa Cruz Biotech Inc.), 10 μl of SPA PVT antibody-binding beads(Amersham Co.), 10 μl of 0.1 μ Ci [$^3H$]propionylated-hShc peptide(Amersham Co.), 10 μl of 6 μg anti-GST rabbit IgG(Molecular Probes) and 10 μl of a DMSO solution containing each of the compounds obtained in Example 2 and the total volume was adjusted to 200 μl using SH2 buffer solution(20 mM Tris-HCl, 250 mM NaCl and 0.1% cow serum albumin, pH 7.4). The resulting mixture(sample) was reacted at room temperature for 30 minutes. After the completion of the reaction, the Grb2-Shc binding inhibiting activity was determined by examining the extent of comparative binding of [$^3H$]propionylated-hShc peptides toward Grb2 proteins, expressed by a unit of count per minute(CPM), with a liquid scintillation counter. The same procedure was repeated in the absence of GST-Grb2 (blank) or in the absence of any added compounds(control).

The Grb2-Shc binding inhibiting activity was then calculated in accordance with the following equation:

$$\text{Degree of Inhibition (\%)} = 100 \times \left[1 - \frac{CPM(sample) - CPM(blank)}{CPM(control) - CPM(blank)}\right]$$

The $IC_{50}$ values of Compounds(I), (II) and (III) were determined to be 6, 12 and 11 μM, respectively.

As the above results show, the azapilone compounds of the present invention possess high inhibiting activity against Grb2-Shc binding, and, therefore, can be used as an anti-cancer agent for suppressing the expression of oncogenic genes and as an agent for preventing and treating intracellular signal transmission-related diseases, for example, asthmas, transmission of cancer, cardiovascular disease and autoimmune disease.

While the embodiments of the subject invention have been described and illustrated, it is obvious that various changes and modifications can be made therein without departing from the spirit of the present invention which should be limited only by the scope of the appended claims.

What is claimed is:

1. The compound of formula(I) which inhibits the bonding between Grb2 and Shc:

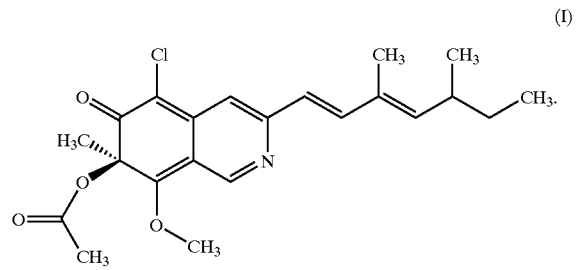
(I)

2. A pharmaceutical composition for treating or preventing an intracellular signal transmission-related disease, comprising a therapeutically effective amount of one or more of the compounds of formulae (I) as an active ingredient, and a pharmaceutically acceptable carrier:

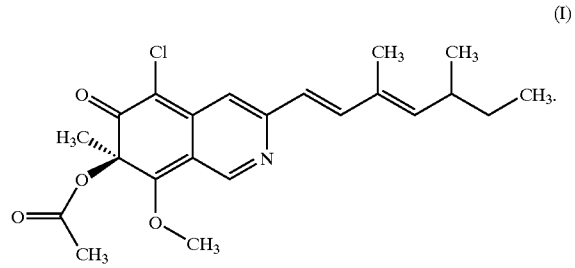
(I)

* * * * *